United States Patent [19]

Morenings

[11] Patent Number: 4,957,480
[45] Date of Patent: Sep. 18, 1990

[54] METHOD OF FACIAL TONING

[75] Inventor: Gerhard H. Morenings, Bristol, Va.

[73] Assignee: Universal Health Products, Inc., Bristol, Va.

[21] Appl. No.: 151,566

[22] Filed: Feb. 2, 1988

[51] Int. Cl.$^5$ .............................................. A61N 1/30
[52] U.S. Cl. ..................................... 604/20; 128/24.2; 128/803; 128/898
[58] Field of Search ............... 128/803, 421, 24.2, 128/24.5, 898; 604/20

[56] References Cited

U.S. PATENT DOCUMENTS

| | | | |
|---|---|---|---|
| 707,508 | 8/1902 | Gibbs | 128/421 |
| 768,581 | 8/1904 | Bulis et al. | 128/421 X |
| 4,324,253 | 4/1982 | Greene et al. | 128/421 |
| 4,406,658 | 9/1983 | Littin et al. | 604/20 |
| 4,465,074 | 8/1984 | Buchalter | 128/803 X |
| 4,583,547 | 4/1986 | Granek et al. | 128/803 X |
| 4,640,689 | 2/1987 | Sibalis | 604/20 |
| 4,702,732 | 10/1987 | Powers et al. | 128/803 X |
| 4,708,716 | 11/1987 | Sibalis | 604/20 |
| 4,712,558 | 12/1987 | Kidd et al. | 128/421 |

*Primary Examiner*—Max Hindenburg
*Assistant Examiner*—J. P. Lacyk
*Attorney, Agent, or Firm*—Malcolm G. Dunn

[57] ABSTRACT

Method of toning the muscles and tissues of the human face by stimulating the motor nerves and hence cause contractions of the muscles of the human face by applying predetermined galvanic currents, frequencies, and polarities through moistened tips of electrodes continually moistened with a liquid solution of positively and negatively charged particles for introduction into the tissues for nourishment of the muscles and surrounding facial tissues.

25 Claims, 9 Drawing Sheets

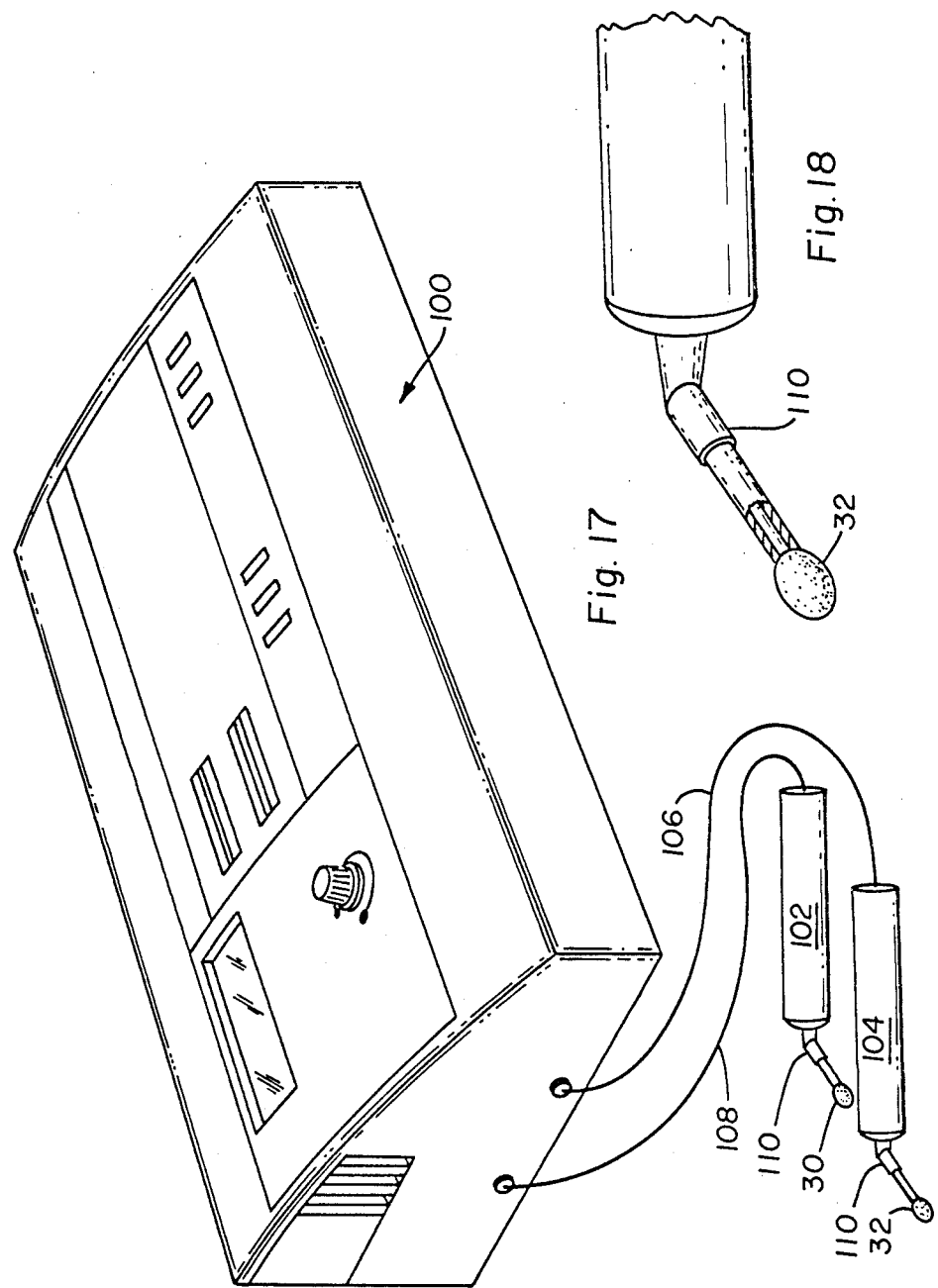

METHOD OF FACIAL TONING

TECHNICAL FIELD

The present invention relates to a method of toning the muscles underlying the human face and nourishing them and the overlying facial tissues through applied galvanic current and liquid solution of positively and negatively charged particles.

BACKGROUND ART

The skin of the human being, for example, is the largest organ and comprises about one-sixth of the total body weight. It protects the human being from ultraviolet rays; from mechanical, chemical and thermal injuries; from bacterial invasions and from dehydration and water penetration.

The skin is also the largest sensory organ, and contains nerve endings for touch, pain, pressure and temperature.

The three main layers of the skin comprise the epidermis, which is dry dead skin, nonvascular; the dermis, which is flexible, elastic and vascular tissue; and the subcutaneous, which is mostly fatty tissues.

The layers of the epidermis comprise the stratum corneum, which is a horny layer, made up of flattened dead cells; the stratum lucidum, which is a thin homogeneous layer; the stratum grandulosum which are granules effecting keratinization; the stratum spinosum, which are cells in the growing process; and the stratum germinativum, which is where new cells are produced and is also the location of melanin, a dark pigment.

The layers of the dermis comprise the stratum papillare, which are small, sensitive vascular papillare; and the stratum reticulare, which is the connective tissue composed of collagen.

Nutrition to the skin is achieved by diffusion from the dermis to the stratum germinativum layer of the epidermis. There are two methods of diffusion: (1) diffusion of a liquid through a cell wall; and (2) diffusion of molecules through cell wall pores. Any substance, such as water, the molecules of which are smaller than the pores, can pass through those pores. The factors that determine the rate of diffusion comprise: (1) concentration gradient, i.e., from higher to lower concentration; (2) pressure gradient, i.e., from higher to lower pressure; and electrical gradient, i.e., ions are attracted or repelled by positive (+) or negative (−) charges and thus, are caused to move across a membrane. The present invention is concerned with the effects of the electrical gradient.

The human body is about one-half muscle and comprises three types of muscles: (1) voluntary-striated, skeletal muscles; (2) involuntary-smooth visceral muscles; and (3) intermediate-cardiac muscles. The present invention is concerned only with the voluntary muscles.

Muscle cells, muscle fibers, grow by enlargement not by cell division. Once a muscle fiber is destroyed it will not regenerate, however, surrounding muscle fibers may enlarge and take over its function. A decrease in muscle size due to lack of use is called "atrophy." If a muscle is re-inervated within three to four months after loss of use, full function can usually be restored, but after four months of disuse muscle fibers begin to die. After about two years of disuse, usually no function can be restored to muscles, and the muscle fibers become restricted by fat and fibrous tissue.

Each muscle fiber contains thousands of myofibrils which run parallel with the muscle fibers and are the contractile elements of the muscle fiber. Each myofibril contains myosin (thick) and actin (thin) filaments which actually cause the contraction. When an impulse for a contraction is received, crossbridges located on the myosin filaments pull like oars causing a creeping motion. Muscle response to an impulse is an "all or nothing" response. Either the impulse is strong enough to cause a contraction in a muscle fiber, or it is not strong enough. If the impulse is strong enough, the contraction will be along the entire length of the muscle fiber. The more muscle fibers that are excited, the stronger the contraction will be.

Each muscle fiber has a neuromuscular function located at the middle of the fiber. This is the point where the nerve fiber connects with the muscle fiber, and therefore, is where a muscle fiber is best stimulated. The purpose of the neuromuscular fiber is to amplify weak impulses so that they are strong enough to cause a contraction. A motor point is a point of excessive excitability. This would be a location where several neuromuscular functions were found very close to each other.

Muscle fibers are individual entities, and can act independently of each other or in conjunction with each other. Muscle fibers run the entire length of the muscle, and are separated from each other by a connective sheath called the endomysium. Muscle fibers are grouped into bundles called fasciculi. These fasciculi are separated from each other by a connective sheath called the perimysium. The fasciculi are grouped together to form muscles. Each muscle is enveloped by a connective tissue called the epimysium. Large blood vessels and nerves enter the muscle through the epimysium, and then begin to divide and branch until they supply every muscle fiber. Every muscle fiber has its own source of nutrition and stimulation. All of the muscle fibers that are stimulated by a single nerve fiber are called a "motor unit." Each motor unit contains an average of 150 muscle fibers.

Muscle tone is the normal degree of tension in a muscle at rest, or the resistance of a muscle to passive elongation or stretch. Muscle tone in the human body is created and maintained by a steady discharge of motor impulses from the brain and feedback from the spinal cord via muscle spindles. The brain, via the central nervous system, sends steady impulses to the muscle causing it to contract. Muscle spindles, which are specialized fibers in the muscle, detect the contraction and send a message to the spinal cord via the peripheral nervous system. The spinal column sends another motor impulse back to the same muscle causing another contraction. This is how tension is maintained in the muscle. As time between the impulses from the brain increases due to age, sickness or accident, the tension or tone in the muscle decreases. There are several factors that can affect muscle tone (some increase it while others decrease it). The following factors will reduce muscle tone: (1) neurologic deficiencies, such as trauma, aging, diseases, and nutritional deficiencies; (2) metabolic deficiencies, such as aging, nutritional deficiencies, and poor circulation; (3) physical effects, such as trauma, stress, environment and lifestyle; and (4) mental effects.

The following factors will increase muscle tone: (1) neurologic support, such as remove interference, physiotherapy, nutrition, and electroneurological stimulation; (2) metabolic support, such as increase circulation by electrostimulation, exercise, nutrition, iontophoresis, and massage; (3) physical support, such as electrotone and exercise tone; and (4) mental support, such as education and positive habits.

The present invention concerns use of galvanic current to increase or maintain muscle tone, and three ways that it accomplishes this is (1) circulation, i.e., nutrition by increasing circulation, the muscles are provided with the nutrients they need to maintain tonus; (2) contractions, i.e., by exciting a nerve with electrical impulses to cause a muscle to contract, the muscle may be tightened or relaxed and thus may be returned to proper tonus; and (3) cerebral effect, i.e., by exciting the nerves of the peripheral nervous system, this results in an imitation of neuro impulses from the brain which create and maintain muscle tone, and via the central nervous system to "remind" the brain to initiate more of those impulses for a period of time.

Strong prolonged contractions in a muscle lead to fatigue because of diminished circulation and metabolic process. Lactic acid is produced in the muscle during activity. Initially, this lactic acid will cause an increase in circulation, and nourishment to the muscle; but if the activity continues, the circulation is not able to remove the lactic acid and it builds up in the muscle interfering with circulation and nourishment. When the muscle does not get nourishment that it needs, it cannot perform the work and will fatigue. In the present invention fatigue is beneficial because it relaxes the muscle.

There are four different types of muscle action. The type of action is determined by the purpose of the movement; therefore, any skeletal muscle can exhibit any of the actions under the right circumstances. These four are: (1) prime mover, the action required to bring about the desired movement; (2) antagonist action, the action opposite to the prime movement, which is required to keep the prime movement smooth and controlled; (3) fixation action, the action required to hold a body part in a fixed position; and (4) synergist action, the action required if the prime mover has an undesired action, it then acts as an antagonist "emergency action."

As heretofore mentioned, this invention concerns only those muscles involving the face and the tissues overlying those muscles. The muscles of facial expression, therefore, are cutaneous lying in the subcutaneous fascia rather than the deep fascia. These muscles attach directly into the skin. Individual muscles seldom remain separate and distinct throughout their length because they merge with neighboring muscles at their attachments.

When a muscle movement occurs usually one end of the muscle stays fixed while the other end moves. The origin of a muscle is its point of fixed attachment. The insertion of a muscle is its point of movable attachment.

Iontophoresis concerns the concept of introducing various ions electrically into tissues through intact skin. It has been used to introduce medications by transporting chemicals across a membrane by using an electric current as the driving force. Generally, a direct current passing through an electrolytic solution causes ions, which are electrically charged particles dissolved or suspended in solution, to migrate according to their electric charge. Positive ions are repelled by a positive pole of the current source and attracted by the negative pole, and negative ions are repelled by the negative pole of the current source and attracted by the positive pole. Passage of the current depends upon this ionic migration, which is called "electrophoresis." Iontophoresis takes advantage of the ionization state of a drug, for instance, to push charged particles past biologic membranes. The charge on the particle is directly related to the chemical nature of the surface of the particle. That nature stems from the chemical reactions or ionization in which positively charged hydrogen ions are distributed between the surface of the particle and the liquid.

Electrical stimulation has been employed to cause contraction of muscles, as in the use of cardiac pacemakers, the treatment of chronic pain, the treatment of urinary and anal incontinence, as well as in other therapeutic applications. Generally, and as heretofore more specifically described, the electrical stimulation excites a nerve causing the propagation of an impulse and thereby evoking a behavioral response in the associated muscle, all in a manner well known.

DISCLOSURE OF THE INVENTION

In accordance with the present invention, I provide a method of toning the muscles and tissues of the human face by stimulating the motor nerves to cause contraction of the muscles of the human face by use of a pair of electrodes connected to a source of predetermined galvanic current and operating at a predetermined frequency and predetermined polarity, and continually moistening the tips of the electrodes with a liquid solution of positively and negatively charged particles and pressing the moistened tips against the skin of the human face at two different positions and while pressed against the skin moving in a predetermined manner at least one of the moistened tips relative to the other to a still different position as the charged particles penetrate into the epidermis and dermis of the human face.

The moistened tips of the electrodes in this method may be pressed firmly against the skin in overlying relation to the middle of a muscle and then the moistened tips ma be moved respectively and simultaneously along the muscle toward the origin and the insertion of the muscle. In this method, the frontalis, corrugator, depressor anguli oris, depressor labii inferiores and mentalis muscles are caused to be stimulated into contraction. Each of the moistened tips may be operated at a galvanic current of about 300 to about 640 microamperes and at a frequency of about 30 to about 99 hertz, and alternating in polarity from positive to negative for a duration of about 1 to about 4 seconds for each of the polarities.

One of the moistened tips of the electrodes in this method may be pressed firmly against the skin at one position overlying one of the ends of a muscle, and the other of the moistened tips may be pressed firmly against the skin at another position at a predetermined location along the muscle and then moving one of the moistened tips along the muscle toward the other of the moistened tips and compressing therebetween a fold of skin for a predetermined period of time, such as about three to about seven seconds, and preferably four seconds. In this method, each of the orbicularis oculi, orbicularis oris and buccinator muscles are caused to be stimulated into contraction. Each of the moistened tips may be operated at galvanic current of about 100 to about 640 microamperes and at a frequency of about 0.5 to about 20 hertz, and alternating in polarity from positive to negative polarity for a duration of about 1 to about 4 seconds for each of the polarities.

In this method, one of the moistened tips may be pressed firmly against the skin at one position overlying the insertion of a muscle and the other of the moistened tips may be pressed firmly against the skin at another position at a predetermined distance along the muscle from the insertion of the muscle, and then moving each of the moistened tips along the muscle toward the other of the moistened tips and compressing therebetween a fold of skin for a predetermined period of time. In this method, each of the temporalis, levator labii superioris, levator labii superioris nasii, zygomaticus minor, zygomaticus major, risorius, and platysma muscles are caused to be stimulated into contractions. Each moistened tip may be pressed firmly against the skin for about four to about eight seconds before moving each of the moistened tips toward the other of the moistened tips. The moistened tips may also compress therebetween a fold of skin for about three to about seven seconds. Each of the moistened tips is operated at a galvanic current of about 100 to about 640 microamperes and at a frequency of about 0.5 to about 20 hertz, and alternating in polarity from positive to negative polarity for a duration of about 1 to about 4 seconds for each of the polarities.

One of the moistened tips in this method may be pressed lightly against the skin at one position and then moved in a linear path, and the other of the moistened tips may be pressed lightly against the skin at another position and closely adjacent to the first mentioned moistened tip and then moved in short brushing movements on the skin back and forth across the aforementioned linear path as the one moistened tip moves along that linear path. Each of the moistened tips may be operated at a galvanic current of about 300 to about 640 microamperes and at a frequency of about 90 to about 100 hertz. In this method, the steps of moving in a linear path and making brushing movements are conducted respectively at positive and negative polarities and then these steps are repeated to be conducted respectively at negative and positive polarities. Each of the moistened tips in this method may be pressed firmly against the skin at one of two different positions across a wrinkle mark in the skin, and then a fold of skin is compressed therebetween for a predetermined period of time. Such predetermined period of time may be about three to about six seconds. Each of the moistened tips may be operated at a galvanic current of about 100 to about 640 microamperes and at a frequency of about 0.5 to about 20 hertz, and alternating in polarity from positive to negative polarity for a duration of about 1 to about 4 seconds for each of the polarities.

In this method one of the moistened tips may be pressed lightly against the skin at one position at about the center of one of the cheeks of the human face, and beginning at the farthest location at another position on the same side of the face where that cheek is located pressing the other of the moistened tips lightly against the skin for a predetermined period of time, such as about three to about seven seconds, at successive spaced intervals in a decreasing spiral path around and toward the aforementioned one of the moistened tips. Each of the moistened tips may be operated at a galvanic current of about 300 to about 640 microamperes and at a frequency of about 90 to about 100 hertz, and alternating in polarity from positive to negative polarity for a duration of about 1 to about 4 seconds for each of the polarities.

One of the moistened tips in this method may be pressed firmly against the skin at one of the two different positions and the other of the moistened tips may be pressed firmly against the skin at the other of the two different positions at a predetermined location from the aforementioned one moistened tip, and then moving one of the moistened tips in a gliding movement toward the other moistened tip and compressing therebetween a fold of skin for a predetermined period of time, such as about three to about seven seconds. Each of the moistened tips is operated at a galvanic current of about 100 to about 640 microamperes and at a frequency of about 0.5 to about 20 hertz, and alternating in polarity from positive to negative polarity for a duration of about 1 to about 4 seconds for each of the polarities.

BRIEF DESCRIPTION OF THE DRAWINGS

The details of my invention will be described in connection with the accompanying drawings, in which

FIG. 17 is a schematic illustration of an apparatus for providing a source of galvanic current connected to a pair of electrodes; and FIG. 18 is a view of a portion of one of the electrodes illustrated in FIG. 17 and showing a partially brokenaway view of the tip of the electrode and how a cotton-wrapped tip may be inserted therein.

BEST MODE FOR CARRYING OUT THE INVENTION

I have discovered through many experiments that certain movements over the skin of the human face with galvanically connected tips (of electrodes) at certain galvanic currents, frequencies, polarities and durations of application, and the tips being continually moistened with a liquid solution of positively and negatively charged particles, will result in the relaxation of some muscles, in the strengthening and tightening of other muscles, and in the nourishment of the muscles and the facial tissues. The result is a method to affect the overall tone and appearance of the human face.

Figure 1:
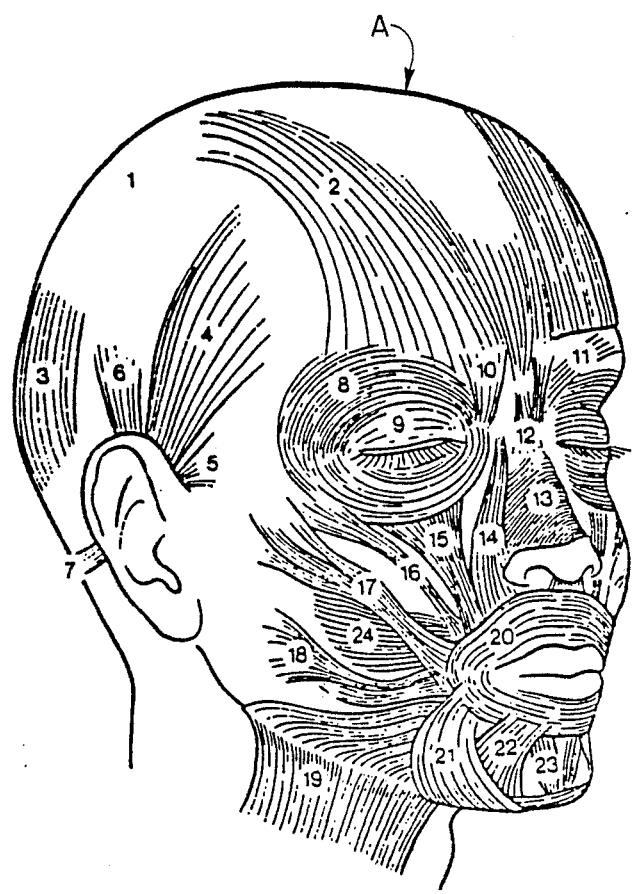
FIG. 1 is a view of the human face with the hair and overlying tissues removed to reveal the underlying muscles of at least one half of the face.

In reference, therefore, to FIG. 1, a human face A is represented with the hair and overlying facial tissues removed to illustrate the underlying muscles controlling the expression of the face. The muscles illustrated are frontalis 2, occipitalis 3, temporalis 4, auricularis anterior 5, auricularis superior 6, auricularis posterior 7, orbicularis oculi (voluntary) 8, orbicularis oculi (involuntary) 9, depressor supercilii 10, corrugator 11, procerus 12, nasalis-compressor naris 13, levator labii superioris nasii 14, levator labii superioris 15, zygomaticus minor 16, zygomaticus major 17, risorius 18, platysma 19, orbicularis oris 20, depressor anguli oris 21, depressor labii inferiores 22, mentalis 23, and buccinator 24.

In reference to the remaining drawing figures, the method herein described is preferably more effectively practiced if the face is appropriately cleansed first. The skin needs to be cleansed to improve conductivity of the galvanic current, absorption of the liquid solutions described herein and to provide more sanitary conditions. Results of the facial toning method are more easily seen without make-up, and the person being treated by this method will become more relaxed. Make-up, for example, may be removed by substances specially formulated for such purpose and without drying the skin. Epidermabrasion solutions may be used to remove dead surface cells and to prepare the skin for reception of other desired substances. The cleansing steps may also include a hot towel steam treatment which tends to open the pores and soften the tissues for better reception of other desired liquid solutions for desired nutritional effects and for increasing circulation. Oils and other impurities may be removed which may still clog the pores but which have been softened by the "steaming" treatment by use, for example, of witch hazel. The latter also serves to act as an antiseptic in case any blemishes are opened.

Apparatus that may be used to apply the galvanic current discussed herein may be a transcutaneous electrical nerve stimulator such as the instrument, FaciaTek 2000, manufactured by the FaciaTek Corporation in Bristol, Virginia. This apparatus is shown schematically in FIG. 17 at 100. This instrument may be adjusted for obtaining different currents, different frequencies and different polarities. The duration of one or the other polarity may be adjusted.

The instrument typically employs two electrodes 102, 104 which are connected by conducting wires 106, 108 to apparatus 100 and a cotton-wrapped tip 30, 32 may be inserted in the tip 110 of each electrode until the cotton portion makes contact with the metal of the electrode, as shown in FIG. 18. The cotton portions are dipped into the desired solution to form moistened tips and are thereafter applied to the skin of the face in the manner of the method described herein. The moistened tips must be kept moist and thus are continually moistened.

In each of FIGS. 2 through 16, the dots 30 and 32 represent the initial positions of moistened tips of the two electrodes, and the arrows 34 illustrate the path and extent of movement of one or both moistened tips relative to a muscle 36 or to the skin of the face. If there is no arrow leading from a dot (moistened tip), then this means that that particular moistened tip remains fixed relative to the skin where initially positioned. It also serves to represent a compression position on one side of a fold 38 of skin that has been compressed between the two moistened tips. FIGS. 7, 10, 12 and 14 illustrate the fold of skin compressed between two moistened tips.

The method described herein involves certain predetermined movements of the moistened tips of the electrodes while pressed against the skin so as to relax certain muscles, strengthen and tighten other muscles and to nourish in general the tissues overlying the muscles.

The amount of galvanic current and frequency is also important to the method, as well as the duration of application and the polarity at which each of the moistened tips of the electrodes is operated.

Tips 30, 32 may be pressed against the skin of the human face at two different positions and at least one of the moistened tips is moved in a predetermined manner relative to the other of the moistened tips to a still different position.

Relaxation

Figure 2:
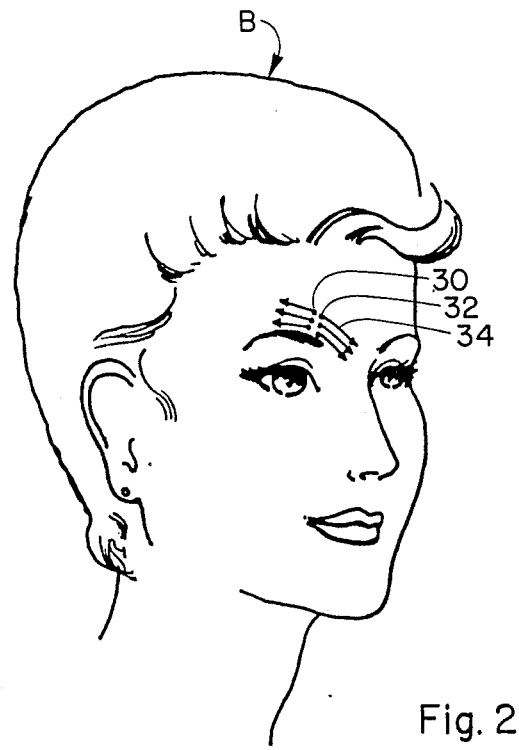
FIG. 2 is a view of a human face illustrating above one of the eyebrows representative movements in that location of the moistened tips, with a dot representing the initial positioning of a moistened tip of an electrode and an arrow illustrating the direction of movement of each moistened tip.
Figure 3:
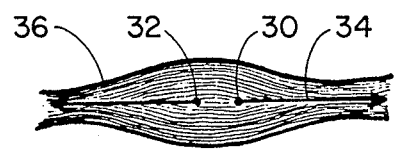
FIG. 3 is a diagrammatic view of a muscle bundle with a dot representing a moistened tip of an electrode and an arrow showing the direction of movement of each moistened tip.
Figure 4:
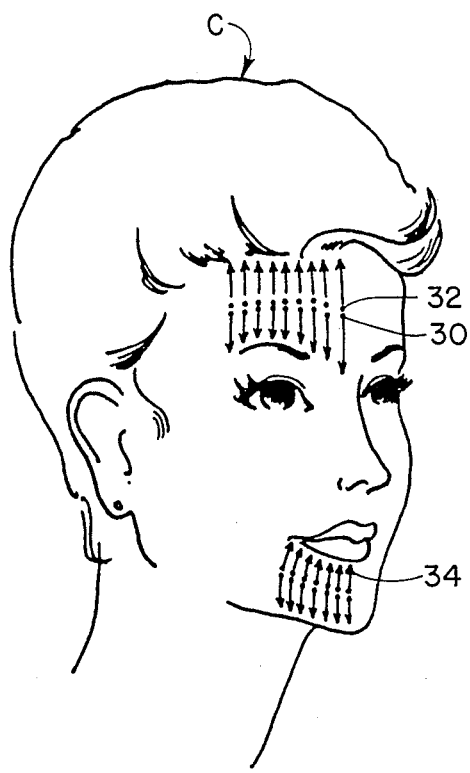
FIG. 4 is a view similar to FIG. 2 except illustrating further different initial positions of moistened tips of electrodes and the direction of movements for the moistened tips.

For instance, in reference to FIGS. 2, 3 and 4 the moistened tips are pressed firmly against the skin of face B and face C in overlying relation to the middle of the muscle 36, and then the moistened tips are respectively and simultaneously moved toward the opposite ends of the muscle or toward the insertion and origin of a muscle. This movement results in a relaxation and thus lengthening of the muscles so treated and in a manner to be described. The actual length of the muscle being treated may be such that its origin lies beyond the face as into the hairline, whereas the insertion or movable end of that muscle will generally be inserted in the face. Therefore, for purposes of this invention, when the movement of the moistened tips is described herein as being "toward the origin," this movement in some instances will not be carried out to the actual origin but only "toward the origin." As will be appreciated, in some cases a full length movement until the muscle origin is reached could undesirably extend into the hairline of the head. The muscles affected, as heretofore mentioned, are the frontalis, the result being to lessen or smooth the forehead lines; the corrugator, the result being to lessen or smooth concentration lines; the depressor anguli oris, the result being to lessen the downward angle of the mouth; the depressor labii inferiores, the result being to lessen or smooth chin lines; and the mentalis, the result being to lessen or smooth chin lines.

The above-described muscles have over the years, depending upon the age of the individual, become tightened and have caused wrinkles and lines in the face, and a drooping of the corners of the mouth. The apparatus 100 for providing the galvanic current is adjusted to produce a current of about 300 to about 640 microamperes at a high frequency of about 30 to about 99 hertz, and alternating in polarity from positive to negative polarity for a duration of about 1 to about 4 seconds, with 2 seconds being preferred, for each of the polarities, so as to cause a build-up of contractions in the muscles without allowing any relaxation between the contractions. In this manner these muscles become fatigued. The duration that the moistened tips are applied to the skin is about 8 to about 12 seconds with 10 seconds being preferred. This length of time and the current and frequency employed will usually not produce any discomfort in the average person and after these muscles have become fatigued in the manner described, they then become relaxed and hence lengthened upon removal of the moistened tips from the skin. The moistened tips of the electrodes, as heretofore described, actually serve to stimulate motor nerves, which in turn generate the desired response of muscle contractions.

Each muscle should be worked for about 10 seconds, and the speed of movement of a moistened tip should be about ¼ inch per second.

Strengthening

Figure 5:
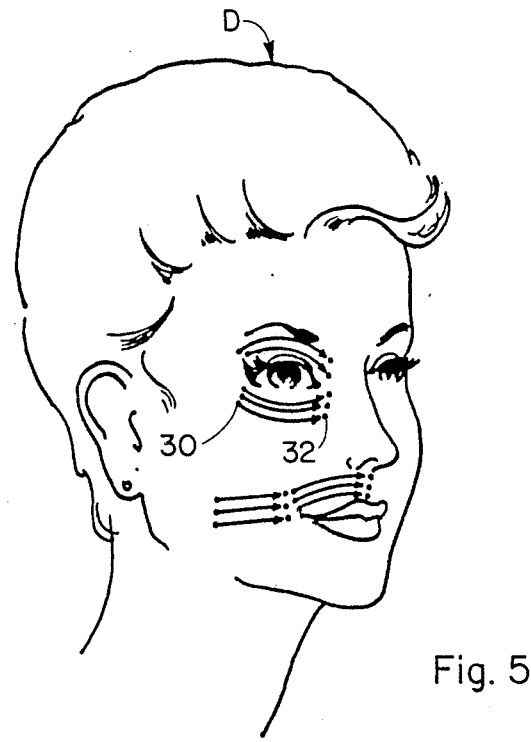
FIG. 5 is a view similar to FIG. 2 except illustrating further different initial positions of moistened tips of electrodes and the direction of movements for the moistened tips.
Figure 6:
FIG. 6 is a view similar to FIG. 3 but illustrating a different movement of one moistened tip and a stationary positioning of the other moistened tip as occur in FIG. 5.
Figure 7:
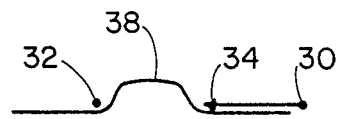
FIG. 7 is a schematic representation of a fold of skin being compressed between two moistened tips as occur in the views of FIG. 5 and FIG. 6.

In reference to FIGS. 5, 6 and 7, one of the moistened tips 30 is pressed firmly against the skin of the face D at one position and the other of the moistened tips 32 is pressed firmly against the skin at another position at a predetermined location along the muscle. Then one of the moistened tips is moved along the muscle (i.e., over the surface of the skin overlying that muscle) toward the other moistened tip and a fold (preferably about one half inch) of skin 38 is compressed therebetween for a predetermined period of time. Each of the moistened tips is operated at a galvanic current of about 100 to about 640 microamperes, and at a frequency of about 0.5 to about 20 hertz. The polarity for each moistened tip is adjusted to alternate from positive to negative polarity for a duration of about 1 to about 4 seconds for each of the polarities. The duration of compression of the fold of skin may be about three to about seven seconds, with four seconds being preferred. As compared to the relaxation procedure above, it will be noted that the frequencies are lower, because the muscles involved in these steps are being strengthened and thus shortened. Any higher frequency would tend to cause undesirable tetanization. The muscles affected are the orbicularis oculi, the results being the reduction of sagging of the tissues over the eyes and puffiness under the eyes, and to lessen or smooth energy lines; the orbicularis oris, the result being to raise the angle of the mouth and smooth pursing lines; and the buccinator, the result being to strengthen it in the interest of overall facial tone since this muscle causes no wrinkling on the human face.

The above-described muscles have over the years, depending upon the age of the individual, become lengthened and have caused sagging of the tissues overlying these muscles.

The speed of movement of a moistened tip should be about ½ inch per second.

Tightening

Figure 8:
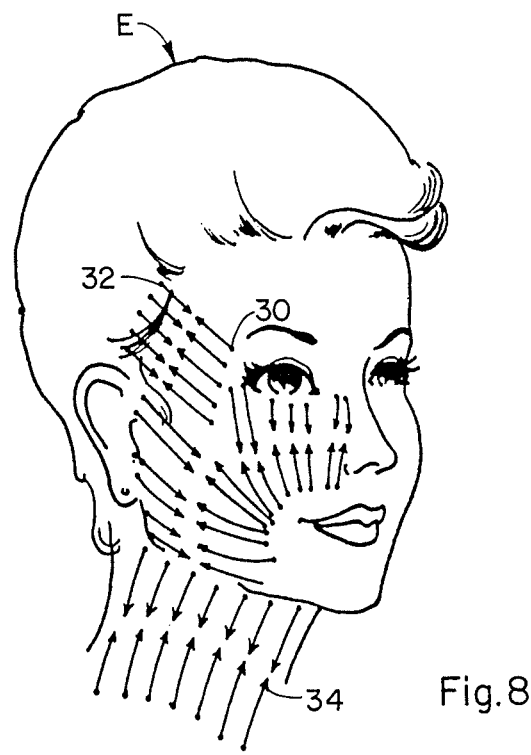
FIG. 8 is a view similar to FIG. 2 except illustrating further different initial positions of moistened tips of electrodes and the direction of movements for the moistened tips.
Figure 9:
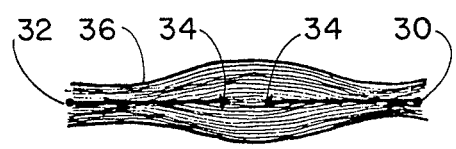
FIG. 9 is a view similar to FIG. 3 but illustrating a different movement of each moistened tip toward the other as occur in FIG. 8.
Figure 10:
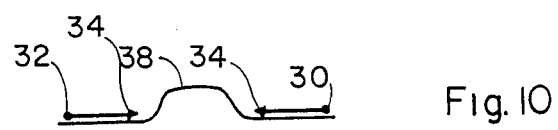
FIG. 10 is a schematic representation of a fold of skin being compressed between two moistened tips as occur in the views of FIG. 8 and FIG. 9.

In reference to FIGS. 8, 9 and 10, one of the moistened tips 30 is pressed firmly against the skin of face E at a position overlying the insertion of the muscle and the other of the moistened tips 32 is pressed firmly against the skin at a position at a predetermined distance along the muscle from the insertion of the muscle. Each of the moistened tips is then moved along the muscle toward the other of the moistened tips causing a fold of skin 38 to be compressed between the two moistened tips, the compression lasting for a predetermined period of time. These steps tend to tighten the muscles. The muscles affected are the temporalis, the result being to lessen or smooth crows feet; the levator labii superioris and levator labii superioris nasii, the result being to raise the angle of the mouth and heighten the cheek area; the zygomaticus minor and zygomaticus major, the results being to heighten the cheek area, lessen or smooth the smile line, laugh line and cheek line, and to raise the angle of the mouth; the risorius, the result being to lessen or smooth the smile line, laugh line, cheek line and jaw line; and the platysma, the results being to lessen sagging around the mouth and jaw and to smooth the neck. These steps tighten and thus shorten the muscles described.

The above-described muscles have over the years, depending upon the age of the individual, become lengthened and have caused wrinkles and sagging in the tissues overlying these muscles.

Each of the moistened tips in the above-described tightening procedure is pressed firmly against the skin for about four to about eight seconds, with six seconds being preferred, before moving each of the moistened tips toward the other of the moistened tips. The fold of skin may be compressed between the moistened tips for about three to about seven seconds, with four seconds being preferred. As in the strengthening procedure described above, each of the moistened tips is operated at a galvanic current of about 100 to about 640 microamperes and at a frequency of about 0.5 to about 20 hertz. The polarity for each moistened tip is adjusted to alternate from positive to negative polarity for a duration of about 1 to about 4 seconds, with 2 seconds being preferred, for each of the polarities.

The speed of movement of a moistened tip should be about ½ inch per second.

Strengthening Dermal Layer

Figure 11:
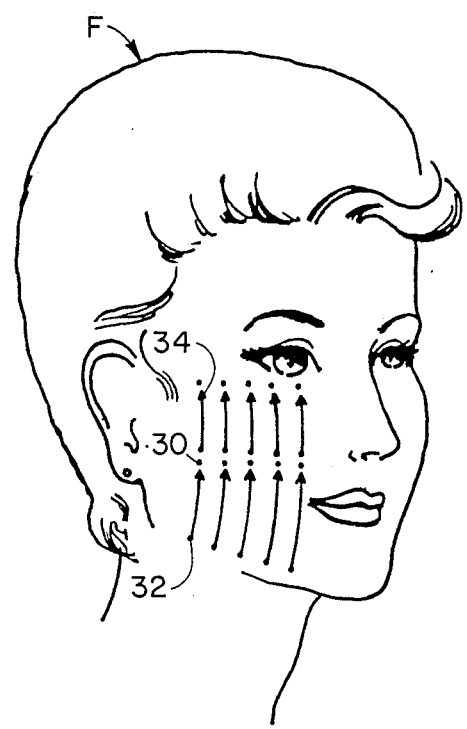
FIG. 11 is a view similar to FIG. 2 except illustrating further different initial positions of moistened tips of electrodes and the direction of movement of one of the moistened tips and the stationary position of the other of the moistened tips.
Figure 12:
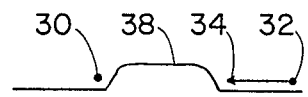
FIG. 12 is a schematic representation of a fold of skin being compressed between two moistened tips as occur in the view of FIG. 11.

In reference to FIGS. 11 and 12, one of the moistened tips 30 is pressed firmly against the skin of face F at one position and the other of the moistened tips 32 is pressed firmly against the skin at another position at a predetermined location from moistened tip 30. Then moistened tip 32, for instance, is moved in a gliding movement toward moistened tip 30, the two moistened tips compressing therebetween a fold 38 of skin for a predetermined period of time, such as about three to about seven seconds, with four seconds being preferred. In these steps the movements of the moistened tips are not necessarily in relation to any particular muscle because the purpose is to strengthen the dermal layer of the skin and to stimulate circulation in that layer of tissue. Each of the moistened tips is operated at a galvanic current of about 100 to about 640 microamperes and at a frequency of about 0.5 to about 20 hertz, and alternating in polarity from positive to negative polarity for a duration of about 1 to about 4 seconds, preferably 2 seconds, for each of the polarities.

The speed of movement of a moistened tip should be about ½ inch per second.

Compressing

Figure 13:
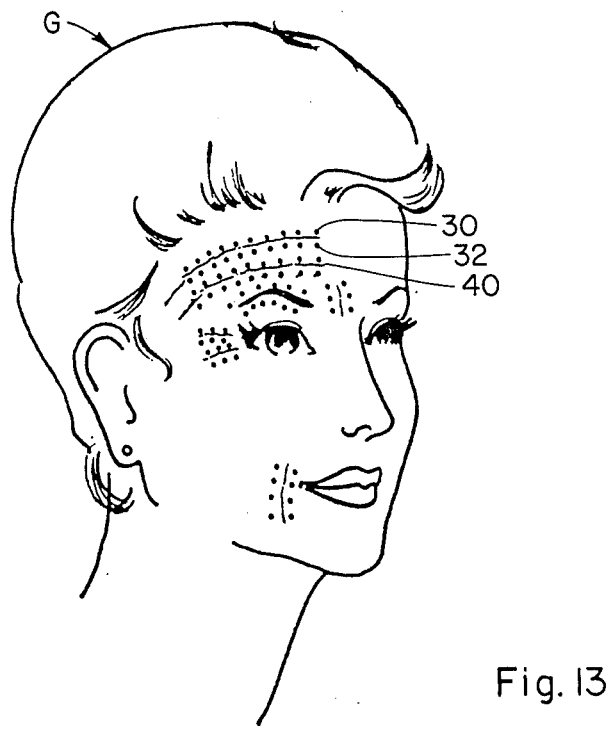
FIG. 13 is a view similar to FIG. 2 except illustrating further different initial positions of moistened tips of electrodes.
Figure 14:
FIG. 14 is a schematic representation of a fold of skin being compressed between two moistened tips as would occur in the view of FIG. 13.

In reference to FIGS. 13 and 14, each of the moistened tips 30, 32 is pressed firmly against the skin of face G at different positions across a wrinkle mark 40 in the skin, and then the moistened tips compress therebetween a fold of skin for a predetermined period of time, such as for about three to about seven seconds, with four seconds being preferred. Each of the moistened tips is operated at a galvanic current of about 100 to about 640 microamperes and at a frequency of about 0.5 to about 20 hertz. The polarity is adjusted to alternate from positive to negative for a duration of about 1 to about 4 seconds for each of the polarities. These steps serve to strengthen the dermal layer of the skin and stimulate circulation in that layer of tissue.

Energizing

Figure 15:
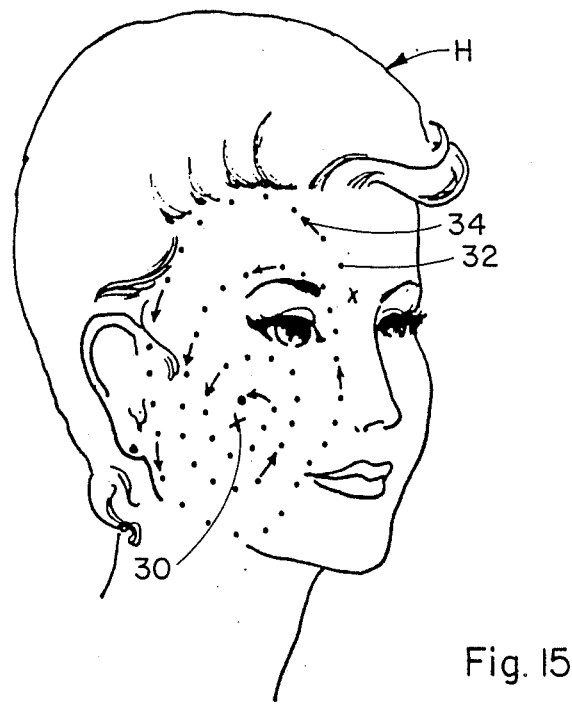
FIG. 15 is a view similar to FIG. 2 except illustrating further different initial positions of moistened tips of electrodes and the direction of movement of one moistened tip relative to a fixed moistened tip as represented by "x" at the middle of the cheek.

In reference to FIG. 15, one of the moistened tips, such as 30, is pressed lightly against the skin of face H at one position at about the center of one of the cheeks of the face. Then beginning at the farthest location on the same side of the face H where the cheek is located, the other moistened tip 32 is pressed lightly against the skin for a predetermined period of time, such as about three to about seven seconds, and preferably four seconds, at successive spaced intervals in a decreasing spiral path around and toward moistened tip 30. These steps tend to energize or stimulate circulation in the epidermal layer of the skin. Each of the moistened tips is operated at a galvanic current of about 300 to about 640 microamperes and at a frequency of about 90 to about 100 hertz, and alternating in polarity from positive to negative polarity for a duration of about 1 to about 4 seconds, preferably 2 seconds, for each of the polarities.

Brushing

Figure 16:
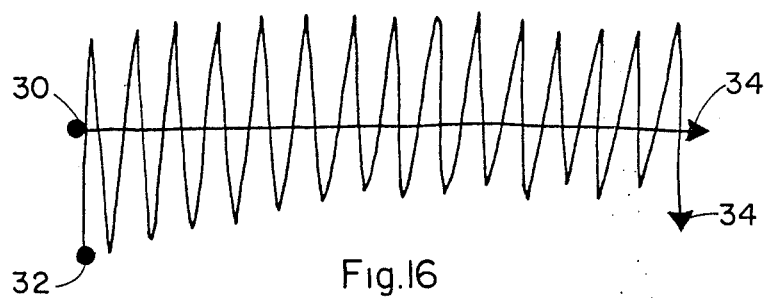
FIG. 16 is a schematic illustration of one moistened tip moving in a linear path and the other moistened tip moving in a brushing movement across the linear path as each moistened tip moves in its respective path closely adjacent the other moistened tip.

In reference to FIG. 16, the schematic diagram illustrates the use of the moistened tips to "brush" the skin to stimulate circulation in the epidermal layer of the skin. For instance, one moistened tip 30 is pressed lightly against the skin at one position and then is moved in a linear path. The other moistened tip 32 is pressed lightly against the skin at another position closely adjacent to moistened tip 30 and is then moved in short brushing movements on the skin back and forth across the aforementioned linear path as moistened tip 30 moves along that linear path. The steps of moving in a linear path and making brushing movements are conducted respectively at positive and negative polarities, and then the steps are repeated to be conducted respectively at negative and positive polarities. Each of the moistened tips is operated at a galvanic current of about 300 to about 640 microamperes and at a frequency of about 90 to about 100 hertz.

Summary

In the steps of the method described herein, the resulting contractions of the muscles described in response to the stimulation of the associated motor nerves (not specifically illustrated herein, but known in the art) results in circulation of blood and hence nourishment of the muscles and associated tissues. The moistened tips, as earlier described, are continually moistened with a liquid solution of positively and negatively charged particles. Various ingredients may be used in such liquid solution, such as collagen, elastin and other active ingredients found naturally in the human body, and which are only being replaced for use by the body. Nutritious substances containing proteins, fats, carbohydrates, water and other trace elements may also be introduced into the tissues by use of the moistened tips in the manner described. Glycerin and other emollients may be introduced. All substances mentioned, and others, not specifically mentioned, may be introduced, depending upon the state of facial tone and extent of aging. All such substances must be ionized so as to be able to penetrate by the concept of iontophoresis into the skin. Liquid solutions that are ionized and therefore penetrated into the epidermis and dermis will have a longer effect than liquid solutions that only stay on the surface of the skin, such as moisturizers.

The invention has been described in detail with particular reference to preferred embodiments thereof, but it will be understood that variations and modifications can be effected within the spirit and scope of the invention.

I claim:

1. The method of toning the muscles and tissues of the human face by stimulating the motor nerves to cause contraction of the muscles of the human face by used of a pair of electrodes connected to a source of predetermined galvanic current and operating at a predetermined frequency and predetermined polarity, said method comprising:

continually moistening the tips of said electrodes with a liquid solution of positively and negatively charged particles and pressing said moistened tips against the skin of said human face at two different positions and while pressed against said skin moving in a predetermined manner at least one of said moistened tips relative to the other to a still different position as the charged particles penetrate into the epidermis and dermis of said face whereby the movement in said predetermined manner results in improved penetration of the charged particles into the epidermis and dermis of said face to further tone the muscles and tissues of the human face.

2. The method as defined in claim 1, and wherein said moistened tips are pressed firmly against said skin in overlying relation to the middle of a muscle and then moving said moistened tips respectively and simultaneously along the muscle toward the origin and the insertion of the muscle.

3. The method as defined in claim 2, and wherein each of the frontalis, corrugator, depressor anguli oris, depressor labii inferiores and mentalis muscles are caused to be stimulated into contraction.

4. The method as defined in claim 1, and wherein one of said moistened tips is pressed firmly against said skin at one of said two different positions and overlying one of the ends of a muscle and the other of said moistened tips is pressed firmly against said skin at the other of said two different positions at a predetermined location along the muscle and moving one of said moistened tips along the muscle toward the other of said moistened tips and compressing therebetween a fold of skin for a predetermined period of time.

5. The method as defined in claim 4, and wherein each of the orbicularis oculi, orbicularis oris and buccinator muscles are caused to be stimulated into contraction.

6. The method as defined in claim 1, and wherein one of said moistened tips is pressed firmly against said skin at one of said positions overlying the insertion of a muscle and the other of said moistened tips is pressed firmly against the skin at the other of said positions at a predetermined distance along the muscle from said insertion of said muscle, and moving each of the moistened tips along the muscle toward the other of said moistened tips and compressing therebetween a fold of skin for a predetermined period of time.

7. The method as defined in claim 6, and wherein each of the temporalis, levator labii superioris, levator labii superioris nasii, zygomaticus minor, zygomaticus major, risorius, and platysma muscles are caused to be stimulated into contractions.

8. The method as defined in claim 6, and wherein each of said moistened tips is pressed firmly against said skin for about four to about eight seconds before moving each of said moistened tips toward the other of said moistened tips.

9. The method as defined in claim 6, and wherein said moistened tips compress therebetween a fold of said skin for about three to about seven seconds.

10. The method as defined in claim 2, and wherein each of said moistened tips is operated at a galvanic current of about 300 to about 640 microamperes, at a frequency of about 30 to about 99 hertz, and alternating in polarity from positive to negative for a duration of about 1 to about 4 seconds for each of said polarities.

11. The method as defined in claim 1, and wherein one of said moistened tips is pressed lightly against said skin at one of said positions and is then moved in a linear path, and the other of said moistened tips is pressed lightly against said skin at the other of said positions and closely adjacent to said one moistened tip and is then moved in short brushing movements on said skin back and forth across said linear path as said one moistened tip moves along said linear path.

12. The method as defined in claim 1, and wherein each of said moistened tips is pressed firmly against said skin at one of said different positions across a wrinkle mark in said skin, and then compressing between said moistened tips a fold of skin for a predetermined period of time.

13. The method as defined in claim 12, and wherein said fold of skin is compressed between said moistened tips for about three to seven seconds.

14. The method as defined in claim 1, and wherein one of said moistened tips is pressed lightly against said skin at one of said positions at about the center of one of the cheeks of the human face, and beginning at the farthest location at the other of said positions on the same side of said face where said cheek is located pressing the other of said moistened tips lightly against said skin for a predetermined period of time at successive spaced intervals in a decreasing spiral path around and toward said one of said moistened tips.

15. The method as defined in claim 11, and wherein each of said moistened tips is operated at a galvanic current of about 300 to about 640 microamperes and at a frequency of about 90 to about 100 hertz.

16. The method as defined in claim 15, and wherein the steps of moving in a linear path and making brushing movements are conducted respectively at positive and negative polarities and then said steps are repeated to be conducted respectively at negative and positive polarities.

17. The method as defined in claim 4, and wherein each of said moistened tips is operated at a galvanic current of about 100 to about 640 microamperes and at a frequency of about 0.5 to about 20 hertz, and alternating in polarity from positive to negative polarity for a duration of about 1 to about 4 seconds for each of said polarities.

18. The method as defined in claim 14, and wherein each of said moistened tips is operated at a galvanic current of about 300 to about 640 microamperes and at a frequency of about 90 to about 100 hertz, and alternating in polarity from positive to negative polarity for a duration of about 1 to about 4 seconds for each of said polarities.

19. The method as defined in claim 12, and wherein each of said moistened tips is operated at a galvanic current of about 100 to about 640 microamperes and at a frequency of about 0.5 to about 20 hertz, and alternating in polarity from positive to negative polarity for a duration of about 1 to about 4 seconds for each of said polarities.

20. The method as defined in claim 1, and wherein one of said moistened tips is pressed firmly against said skin at one of said two different positions and the other of said moistened tips is pressed firmly against said skin at the other of said two different positions at a predetermined location from said one moistened tip and moving one of said moistened tips in a gliding movement toward the other moistened tip and compressing therebetween a fold of skin for a predetermined period of time.

21. The method as defined in claim 4, and wherein said moistened tips compress therebetween a fold of said skin for about three to about seven seconds.

22. The method as defined in claim 6, and wherein each of said moistened tips is operated at a galvanic current of about 100 to about 640 microamperes and at a frequency of about 0.5 to about 20 hertz, and alternating in polarity from positive to negative polarity for a duration of about 1 to about 4 seconds for each of said polarities.

23. The method as defined in claim 14, and wherein said other moistened tip is pressed lightly against said skin for about three to about seven seconds before being moved to the next successive spaced interval.

24. The method as defined in claim 20, and wherein said moistened tips compress therebetween a fold of said skin for about three to about seven seconds.

25. The method as defined in claim 20, and wherein each of said moistened tips is operated at a galvanic current of about 100 to about 640 microamperes and at a frequency of about 0.5 to about 20 hertz, and alternating in polarity from positive to negative polarity for a duration of about 1 to about 4 seconds for each of said polarities.

* * * * *